United States Patent [19]

Lohner et al.

[11] Patent Number: 4,690,823
[45] Date of Patent: Sep. 1, 1987

[54] IBUPROFEN-CONTAINING SOFT GELATIN CAPSULES AND PROCESS FOR PREPARING SAME

[75] Inventors: Manfred Lohner; Klaus Posselt, both of Bonn, Fed. Rep. of Germany

[73] Assignee: Dolorgiet Beteiligungs-GmbH, St. Augustin, Fed. Rep. of Germany

[21] Appl. No.: 709,727

[22] Filed: Mar. 8, 1985

[30] Foreign Application Priority Data

Oct. 13, 1984 [DE] Fed. Rep. of Germany ....... 3437599

[51] Int. Cl.⁴ .................. A61K 31/19; A61K 9/48
[52] U.S. Cl. ................. 424/456; 424/455; 514/570; 514/789; 514/960; 514/962
[58] Field of Search ............ 514/570, 789, 960, 962; 424/37

[56] References Cited

U.S. PATENT DOCUMENTS

| | | | |
|---|---|---|---|
| 4,145,440 | 3/1979 | Fitch et al. | 514/770 |
| 4,278,633 | 7/1981 | Fujii | 424/37 |
| 4,361,580 | 11/1982 | Peck et al. | 514/777 |
| 4,428,927 | 1/1984 | Ebert et al. | 424/37 |
| 4,473,584 | 9/1984 | Heckler | 514/570 |
| 4,540,602 | 9/1985 | Motoyama et al. | 424/37 |
| 4,555,524 | 11/1985 | Gruber et al. | 514/570 |

FOREIGN PATENT DOCUMENTS

| | | | |
|---|---|---|---|
| EP70714 | 1/1983 | European Pat. Off. | 514/570 |
| 3437599 | 4/1986 | Fed. Rep. of Germany | 514/570 |

*Primary Examiner*—Ronald W. Griffin
*Attorney, Agent, or Firm*—Wegner & Bretschneider

[57] ABSTRACT

Soft gelatin capsules containing a solution of from 15 to 30 parts by weight of ibuprofen in from 70 to 85 parts by weight of polyoxyethylene-polyoxypropylene polymer or in a mixture of from 30 to 76 parts by weight of polyalkylene glycol and from 7 to 40 parts by weight of a surfactant have a very rapid and high bio-availability of the active ingredient. The active ingredient is not re-precipitated therefrom by aqueous media such as artificial gastric juice.

18 Claims, 8 Drawing Figures

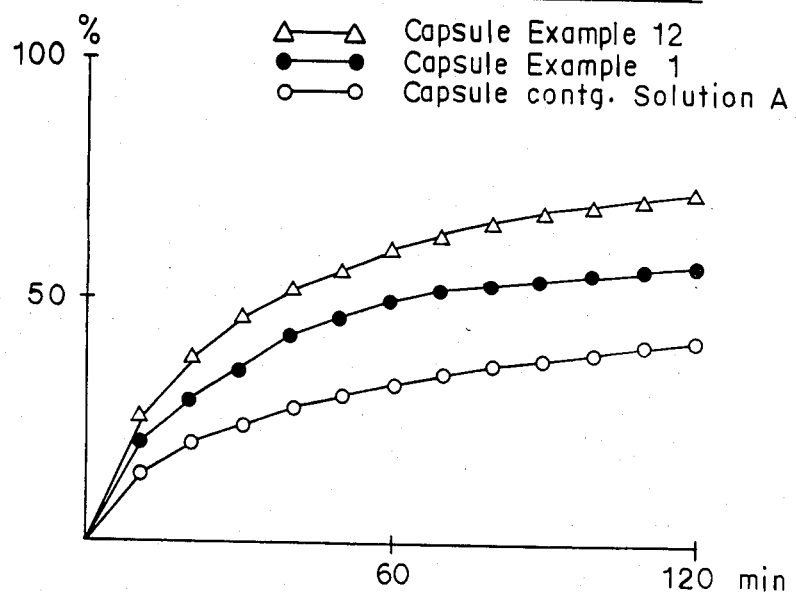
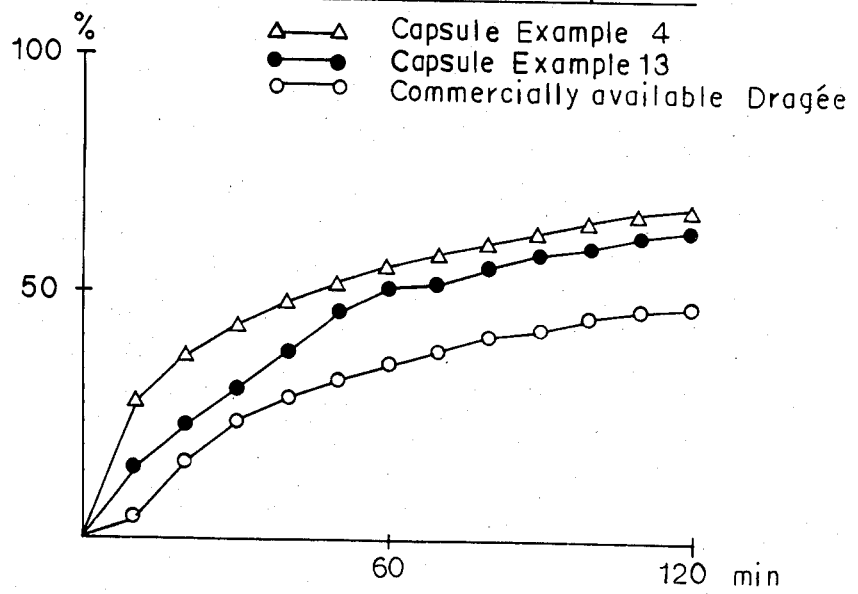

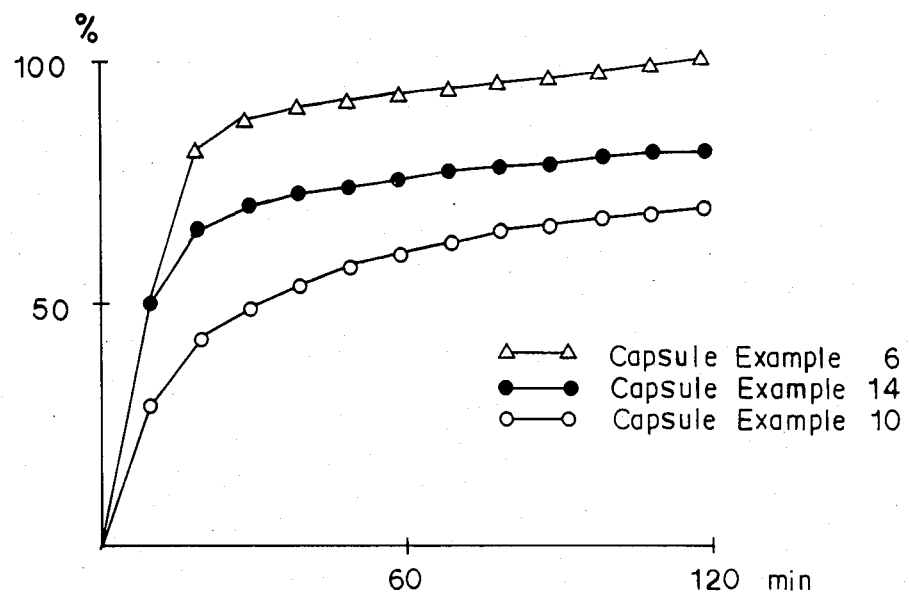
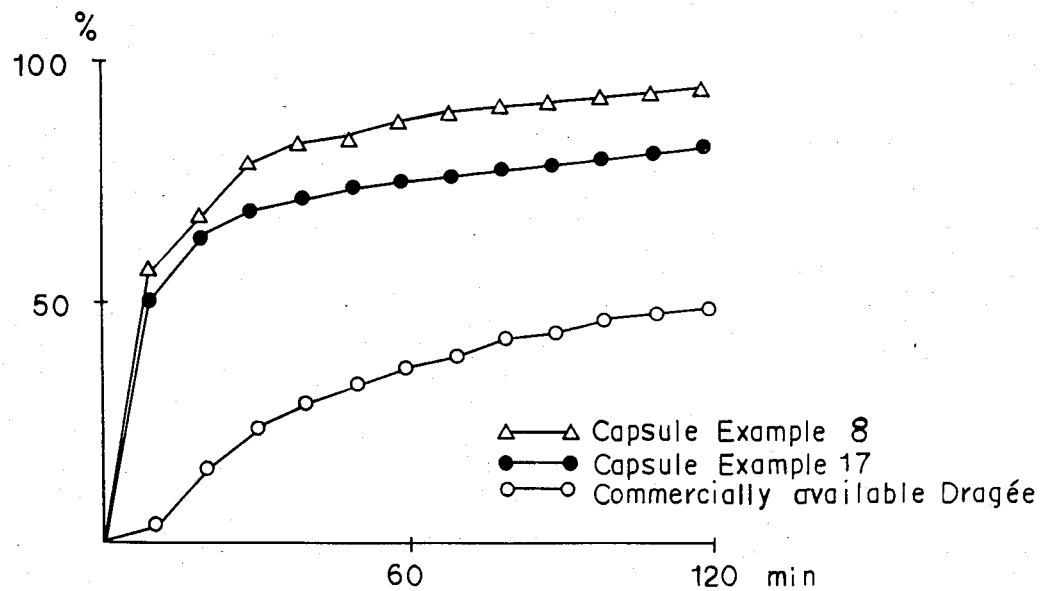

Fig. 2: Blood Level after Intake of 200mg of Ibuprofen
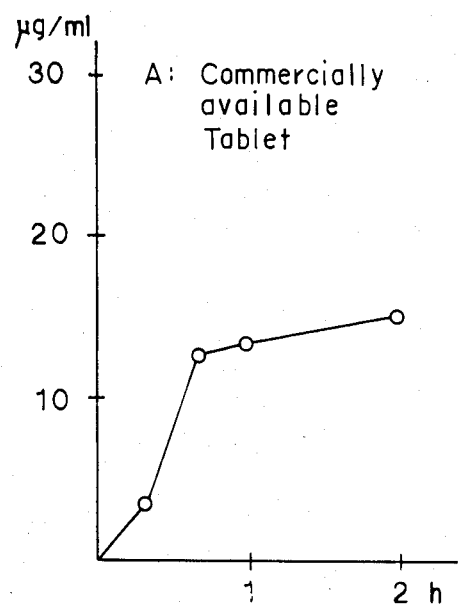
A: Commercially available Tablet
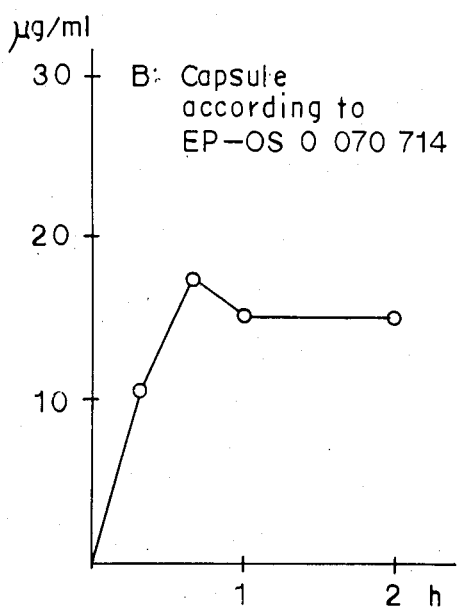
B: Capsule according to EP-OS 0 070 714
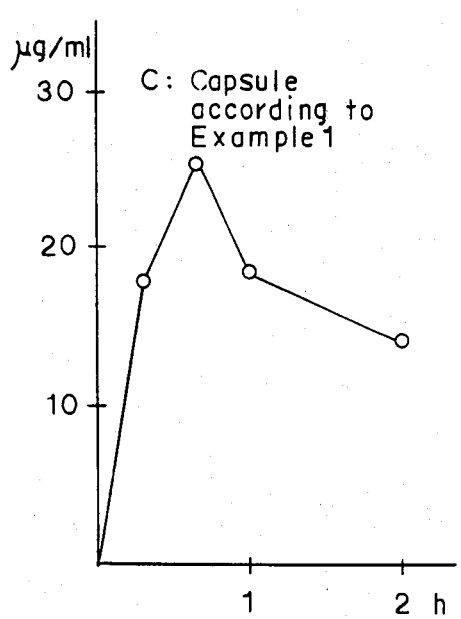
C: Capsule according to Example 1
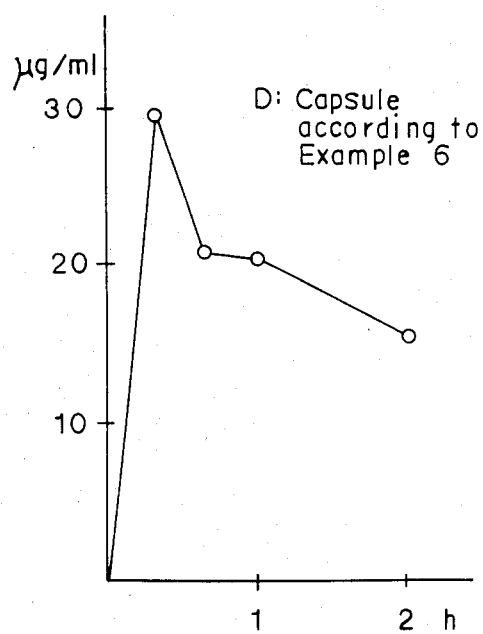
D: Capsule according to Example 6

IBUPROFEN-CONTAINING SOFT GELATIN CAPSULES AND PROCESS FOR PREPARING SAME

BACKGROUND OF THE INVENTION

The present invention relates to soft gelatin capsules containing ibuprofen and a process for preparing same.

The compound ibuprofen, 2-(4-isobutylphenyl)propionic acid, has been known, e.g. from Martindale, the Extra Pharmacopoeia, 28th Edition, 1982, p. 256, as a drug which has anti-inflammatory and analgesic properties. It is used for the treatment of rheumatoid arthritis or other inflammatory diseases of joints, soft tissue rheumatism and gout. Ibuprofen, because of its analgesic properties, has also been widely used as an anodyne, e.g. against pain or discomfort associated with headache, toothache, or menstruation.

A medicament suitable to combat acute pain is demanded to display its effects fast which action, in turn, is only achieved by a quick release and good bio-availability of the active ingredient.

DISCUSSION OF THE PRIOR ART

Ibuprofen for an enteral administration so far has only been commercially available in solid form as a dragee or coated tablet. German Published Unexamined Patent Application (Offen-legungsschriften) Nos. 28 32 380 and 31 24 014 describe liquid suspensions wherein ibuprofen is present in aluminum salt form. Due to the composition and the volume to be taken to receive an effective dose of ibuprofen, these suspensions are not suitable for incorporation in a capsule. German Offenlegungsschrift No. 33 40 347 and European Offenlegungsschrift No. 0 070 714 describe, in addition to other dosage forms, soft gelatin capsules containing ibuprofen suspended in a carrier. High standards have to be met for all of these dosage forms as to the physical properties of the active ingredient such as particle size and specific surface area in order to ensure good availability of ibuprofen. It is for the commercial forms (tablets, dragees) in particular that the conditions of preparation must be strictly observed, as minor alterations in production procedures such as mixing, pressure of compression, and type of machine will affect the physical properties of the particles of the active ingredient and will deteriorate its bio-availability.

It is an object of the present invention to provide a medicament that can be readily taken that contains an active amount of ibuprofen in a carrier, that is simple to prepare and that will quickly display a high activity. Ibuprofen, although it is soluble in some physiologically compatible solvents, will immediately precipitate upon the addition of small amounts of water or when the solution is introduced into an aqueous medium such as, e.g., an artificial gastric juice. When such a solution, upon oral administration, gets into the stomach, then the aqueous content of the stomach causes the ibuprofen to be precipitated so that it will be barred from a quick resorption.

DESCRIPTION OF THE INVENTION

It has now been found that ibuprofen may be readily dissolved in polyoxyethylene-polyoxypropylene polymer or in a mixture of a polyalkylene glycol and a surfactant at a temperature of from 45° C. to 65° C. and will remain in solution upon cooling to room temperature. It has further been found that, surprisingly, no precipitation occurs when these solutions are introduced into an aqueous medium, more specifically into artificial gastric juice, so that the ibuprofen can be quickly and completely resorbed from this solution. In addition, these solutions may be incorporated in soft gelatin capsules in a per se known manner. The latter dosage form has an advantage over all other previously known dosage forms for ibuprofen that upon intake the active ingredient is quickly resorbed. To this effect it is not necessary that, subsequent to synthesis, the active ingredient is subjected to expensive galenic processing measures. Nevertheless, a high bio-availability is achieved with a high degree of reliability and reproducibility and, hence, a fast and reliable display of its effects.

The effects according to the invention, more particularly, are attained when that the ibuprofen-containing soft gelatin capsules contain a solution of from 15 to 30 parts by weight of ibuprofen in 85 to 70 parts by weight of polyoxyethylene-polyoxypropylene polymer or in a mixture of 76 to 30 parts by weight of polyalkylene glycol and 7 to 40 parts by weight of a surfactant. For easier processability and increase of solubility, up to 3 parts of 1,2-propylene glycol may be added without deteriorating the properties as shown upon contacting with an aqueous medium such as artificial gastric juice.

Another advantage of the solutions used in the present invention is that there may be additionally suspended therein up to 40 parts by weight of ibuprofen, so that dosage forms are obtained that, even in the case of high doses, may be of relatively small dimensions and, thus, may be readily administered. This dosage form, more specifically, can be used for the treatment of rheumatic diseases.

According to the invention, a suitable solvent above all is a polyoxyethylene-polyoxypropylene polymer. Said polymer is preferred to have a relative molecular weight of from 1,400 to 2,000. Such products are commercially available, for example under the trade mark Pluronic$^{(R)}$. They are physiologically compatible and, therefore, suitable as agents for the preparation of soft gelatin capsules.

Further suitable solvents include mixtures of 30 to 76 parts by weight of a polyalkylene glycol and 7 to 40 parts by weight of a surfactant. Polyethylene glycol and polypropylene glycol are preferred and their relative molecular weights should preferably be in the range between 300 and 630. These products are also commercially available, physiologically compatible and, therefore, usable for the purpose according to the invention. When polyalkylene glycols are used, it is necessary to additionally employ from 7 to 40 parts by weight of a surfactant in order to prevent reprecipitation of the active ingredient by the aqueous medium such as artificial gastric juice. Preferred suitable surfactants include, for example, polyoxyethyleneglycerol trihydroxystearate, polyoxyethylene ($C_{12-18}$)-fatty alcohol ethers, polyoxyethylene stearate, polyoxyethylenesorbitan mono($C_{12-18}$)-fatty acid esters, and also polyoxyethylene-polyoxypropylene polymer. The number of ethylene oxide units of the polyoxyethyleneglycerol trihydroxystearate should preferably be between 35 and 65 and that of the polyoxyethylene ($C_{12-18}$)-fatty alcohol ethers should preferably be between 15 and 25. The number of ethylene oxide units of the polyoxyethylene stearate should preferably be 15 to 45, and that of the polyoxyethylenesorbitan mono($C_{12-18}$)-fatty acid esters should preferably be between 15 and 25.

In order to dissolve ibuprofen in the solvents according to the invention, the solvents are heated at 45° C. to 65° C., since only at these temperatures the dissolution will take place sufficiently fast. Upon cooling to room temperature, no reprecipitation occurs. If it is desired to incorporate further amounts of ibuprofen in the soft gelatin capsule, the active ingredient may be suspended in the solution at room temperature. It is readily possible that 40 parts by weight are additionally suspended in said solutions at room temperature and thereafter incorporated in soft gelatin capsules. If mixtures of polyalkylene glycol and a surfactant are to be used, then these components are homogeneously mixed together at a temperature of up to 80° C., and the mixture is cooled to about 50° C. to 60° C. At the latter temperature, the ibuprofen is added and dissolved.

Thus, under a second aspect of the present invention, there is provided a process for preparing the ibuprofen-containing soft gelatin capsules as described above, which process is characterized in that from 15 to 30 parts by weight of ibuprofen are dissolved at a temperature of between 45° C. and 65° C. in from 70 to 85 parts by weight of polyoxyethylene-polyoxypropylene polymer or in a mixture of from 30 to 76 parts by weight of polyalkylene glycol and from 7 to 40 parts by weight of a surfactant, the solution is cooled to room temperature and then incorporated in soft gelatin capsules in a per se known manner.

A third aspect of the present invention relates to the use of solutions containing from 15 to 30 parts by weight of ibuprofen in from 70 to 85 parts by weight of polyoxyethylene-polyoxypropylene polymer or in a mixture of from 30 to 76 parts by weight of polyalkylene glycol and from 7 to 40 parts by weight of a surfactant in the preparation of soft gelatin capsules.

The following non-limiting examples serve to further illustrate the soft gelatin capsules and the process for preparing same according to the invention.

EXAMPLE 1

A mixture of 270.62 g of polyethylene glycol 400, 29.26 g of polyoxyethylene-(40)-glycerol trihydroxystearate (Cremophor$^{(R)}$ RH 40; BASF) and 6.12 g of 1,2-propylene glycol is prepared with stirring at from 70° C. to 80° C. The mixture is cooled to 50° C., and 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 2

A mixture of 264.50 g of polyethylene glycol 400 and 29.26 g of polyoxyethylene-(40)-glycerol trihydroxystearate (Cremophor$^{(R)}$ RH 40; BASF) is prepared with stirring at from 70° C. to 80° C. The mixture is cooled to 50° C., and 90.00 g of ibuprofen and, thereafter, 12.24 g of 1,2-propylene glycol are added portionwise thereto with stirring. The solution is cooled to room temperature and then incorporated in soft gelatin capsules of a suitable size. 0.880 g of the solution contain 200 mg of ibuprofen.

EXAMPLE 3

Ibuprofen (90.00 g) is dissolved with stirring at 50° C. to 60° C. in 224.74 g of polyethylene glycol 400, and at said temperature there are added with stirring, in sequence, 24.86 g of polyoxyethylene-(40)-glycerol trihydroxystearate (Cremophor$^{(R)}$ RH 40; BASF) and 10.40 g of 1,2-propylene glycol. The solution is cooled to room temperature and then incorporated in soft gelatin capsules of a suitable size. 0.778 g of the solution contain 200 mg of ibuprofen.

EXAMPLE 4

A mixture of 270.62 g of polypropylene glycol 425, 29.26 g of polyoxyethylene-(40)-glycerol trihydroxystearate (Cremophor$^{(R)}$ RH 40; BASF) and 6.12 g of 1,2-propylene glycol is prepared with stirring at from 70° C. to 80° C. The mixture is cooled to 50° C., and 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 5

A mixture of 270.70 g of polyethylene glycol 600, 29.30 g of polyoxyethylene-(40)-glycerol trihydroxystearate (Cremophor$_{(R)}$ RH 40; BASF) and 6.00 g of 1,2-propylene glycol is prepared with stirring at from 60° C. to 70° C. The mixture is cooled to 50° C., and 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 6

A mixture of 30.773 kg of polyoxyethylene-polyoxypropylene polymer 1900 (Pluronic$^{(R)}$ L 35, Wyandotte Chemicals Corp.), 3.325 kg of polyoxyethylene-(40)-glycerol trihydroxystearate (Cremophor$^{(R)}$ RH 40; BASF) and 0.675 kg of 1,2-propylene glycol is prepared with stirring at 60° C., and 10.227 kg of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 7

A mixture of 391.24 of polyoxyethylene-polyoxypropylene polymer 1500 (Pluronic$^{(R)}$ L 42, Wyandotte Chemicals Corp.), 39.18 g of polyoxyethylene-(40)-glycerol trihydroxystearate (Cremophor$^{(R)}$ RH 40; BASF) and 9.00 g of 1,2-propylene glycol is prepared with stirring at 60° C., and 90.00 g of ibuprofen are added portionwise thereto with stirring. The solution is cooled to room temperature and then incorporated in soft gelatin capsules of a suitable size. 0.882 g of the solution contain 150 mg of ibuprofen.

EXAMPLE 8

A mixture of 276.73 g of polyoxyethylene-polyoxypropylene polymer 1900 (Pluronic$^{(R)}$ L 35, Wyandotte Chemicals Corp.) and 29.77 g of polyoxyethylene-(40)-glycerol trihydroxystearate (Cremophor$^{(R)}$ RH 40; BASF) is prepared with stirring at 60° C., and 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 9

90.00 g of ibuprofen are portionwise added with stirring at 60° C. in 306.00 g of polyoxyethylene-polyoxypropylene polymer 1900 (Pluronic$^{(R)}$ L 35, Wyandotte Chemicals Corp.). The solution is cooled to room temperature and then incorporated in soft gelatin capsules of a suitable size. 0.880 g of the solution contain 200 mg of ibuprofen.

EXAMPLE 10

90.00 g of ibuprofen are portionwise added with stirring at 60° C. in 306.00 g of polyoxyethylene-polyoxypropylene polymer 1500 (Pluronic$^{(R)}$ L 42, Wyandotte Chemicals Corp.). The solution is cooled to room temperature and then incorporated in soft gelatin capsules of a suitable size. 0.880 g of the solution contain 200 mg of ibuprofen.

EXAMPLE 11

90.00 g of ibuprofen are portionwise added with stirring at 60° C. in 306.00 g of polyoxyethylene-polyoxypropylene polymer 2000 (Pluronic$^{(R)}$ L 44, Wyandotte Chemicals Corp.). The solution is cooled to room temperature and then incorporated in soft gelatin capsules of a suitable size. 0.880 g of the solution contain 200 mg of ibuprofen.

EXAMPLE 12

A mixture of 149.94 g of polyethylene glycol 400, 149.94 g of polyoxyethylene-polyoxypropylene polymer 1900 (Pluronic$^{(R)}$ L 35, Wyandotte Chemicals Corp.) and 6.12 g of 1,2-propylene glycol is prepared with stirring at 60° C. to 70° C., and 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 13

A mixture of 270.62 g of polyethylene glycol 400, 29.26 g of polyoxyethylene-(20)-stearyl alcohol (BRIJ$^{(R)}$ 78, Atlas Chemical Industries) and 6.12 g of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 14

A mixture of 270.62 g of polyoxyethylene-polyoxypropylene polymer 1900 (Pluronic$^{(R)}$ L 35, Wyandotte Chemicals Corp.), 29.26 g of polyoxyethylene-(30)-stearate (MYRJ$^{(R)}$ 51, Atlas Chemical Industries) and 6.12 g of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 15

A mixture of 270.62 g of polyoxyethylene-polyoxypropylene polymer 1900 (Pluronic$^{(R)}$ L 35, Wyandotte Chemicals Corp.), 29.26 g of polyoxyethylene-(20)-stearyl alcohol (BRIJ$^{(R)}$ 78, Atlas Chemical Industries) and 6.12 g of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 16

A mixture of 270.62 g of polyethylene glycol 400, 29.26 g of polyoxyethylene-(60)-glycerol trihydroxystearate (Cremophor$^{(R)}$ RH 60; BASF) and 6.12 g of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 17

A mixture of 270.62 g of polyoxyethylene-polyoxypropylene polymer 1900 (Pluronic$^{(R)}$ L 35, Wyandotte Chemicals Corp.), 29.26 g of polyoxyethylene-(60)-glycerol trihydroxystearate (Cremophor$^{(R)}$ RH 60; BASF) and 6.12 of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 18

A mixture of 270.62 g of polyoxyethylene-polyoxypropylene polymer 1500 (Pluronic$^{(R)}$ L 42, Wyandotte Chemicals Corp.), 29.26 g of polyoxyethylene-(20)-sorbitan monostearate (Tween$^{(R)}$ 60, Atlas Chemical Industries) and 6.12 g of 1,2-propylene glycol is prepared with stirring at 60° C. to 70° C., and, after cooling to 50° C., 90.00 g of ibuprofen are added portionwise thereto with stirring. The solution is cooled to room temperature and then incorporated in soft gelatin capsules of a suitable size. 0.880 g of the solution contain 200 mg of ibuprofen.

EXAMPLE 19

A mixture of 270.62 g of polyoxyethylene-polyoxypropylene polymer 1900 (Pluronic$^{(R)}$ L 35, Wyandotte Chemicals Corp.), 29.26 g of polyoxyethylene-(40)-glycerol trihydroxystearate (Cremophor$^{(R)}$ RH 40; BASF) and 6.12 g of 1,2-propylene glycol is prepared with stirring at 60° C. to 70° C., and, after cooling to 50° C., 90.00 g of ibuprofen are added portionwise thereto with stirring. In said solution there are suspended at a temperature of 15° C. to 20° C. another 90.00 g of finely divided ibuprofen. The suspension thus obtained is then incorporated in soft gelatin capsules of a suitable size. 1.080 g of the suspension contain 400 mg of ibuprofen.

The release of ibuprofen from the soft gelatin capsules was tested by dissolution test according to U.S.P. XX, 5th Suppl., in 4 liters of artificial gastric juice without pepsin according to U.S.P. XX. The concentration of ibuprofen was determined by UV spectrometry at 231 nm. For comparison there were used a commercially available dragee and the solutions A and B. 0.880 g of the solution A contain 200 mg of ibuprofen, 666.4 mg of propylene glycol 400 and 13.6 mg of 1,2-propylene glycol. 0.880 g of the solution B contain 200 mg of ibuprofen and 680.0 mg of propylene glycol 400.

The rates of ibuprofen release (percent) of the soft gelatin capsules according to the invention and of the comparative preparations are listed in Table 1.

FIGS. 1A through 1D, in addition to Table 1, also show release over time from some representative dosage forms. It is readily apparent therefrom that ibuprofen is released essentially faster from the soft gelatin capsules according to the invention than from the commercially available dragee and from the capsules containing the comparative solution. Moreover, the ibuprofen release from the comparative preparation comes to a standstill at less than 48% after 2 hours, whereas from the preparations according to the invention it reaches values up to 100%.

TABLE 1

| Preparation | Release of ibuprofen (%) after minutes | | | | |
|---|---|---|---|---|---|
| | 10 | 20 | 30 | 60 | 120 |
| Commercial dragee | 3.7 | 15.0 | 23.7 | 36.2 | 48.7 |
| Capsule containing | | | | | |
| Solution A | 13.7 | 20.0 | 23.7 | 32.5 | 42.5 |
| Solution B | 16.2 | 22.5 | 27.5 | 37.5 | 47.5 |
| Capsule according to | | | | | |
| Example 1 | 20.0 | 28.7 | 35.0 | 50.0 | 58.7 |
| Example 4 | 27.5 | 37.5 | 43.7 | 56.2 | 68.7 |
| Example 5 | 20.0 | 31.2 | 40.0 | 55.9 | 68.2 |
| Example 6 | 50.0 | 81.2 | 87.5 | 92.5 | 100.0 |
| Example 8 | 56.2 | 67.0 | 78.7 | 87.5 | 94.7 |
| Example 9 | 27.5 | 41.2 | 48.7 | 61.2 | 72.5 |
| Example 10 | 28.7 | 42.5 | 48.7 | 60.0 | 70.0 |
| Example 11 | 21.2 | 37.5 | 46.2 | 61.2 | 73.0 |
| Example 12 | 28.7 | 42.5 | 48.7 | 60.0 | 72.9 |
| Example 13 | 21.2 | 37.5 | 46.2 | 61.2 | 64.1 |
| Example 14 | 50.0 | 65.0 | 70.0 | 75.0 | 81.0 |
| Example 15 | 40.0 | 56.2 | 63.7 | 75.0 | 83.7 |
| Example 16 | 13.7 | 22.5 | 30.0 | 51.2 | 60.0 |
| Example 17 | 50.0 | 62.5 | 68.7 | 75.0 | 82.5 |
| Example 18 | 58.7 | 67.5 | 70.0 | 75.0 | 78.2 |

The bio-availability of the ibuprofen from the capsules according to the invention, from a commercially available dragee and from a capsule according to EP-OS No. 0 070 714 (Example 2) was tested with four volunteer test persons. The test persons were administered a capsule or dragee, respectively, each containing 200 mg of ibuprofen; after defined periods of time, blood samples were taken from the test persons, and the contents of ibuprofen in the blood was determined. The average values of the results obtained in said determinations are shown in FIGS. 2A through 2D.

The bio-availability of a drug from a preparation is understood to denote the velocity with and extent to which said medicament will be transferred into the blood circulation (E. Mutschler, Arzneimittel-Wirkungen, Wissenschaftliche Verlagsgesellschaft mbH, Stuttgart 1981). According to F.H. Dost (Grundlagen der Pharmakokinetik, Georg Thieme Verlag, Stuttgart 1968), the area encompassed by the blood level curve and the time axis (AUC=area under the curve) corresponds to the amount of substance in the organism. Therefrom arises the possibility of comparing the bio-availability of a substance released from various forms of application. From the curves of the blood level variations with time as shown in FIGS. 2A through 2D there have been calculated the AUC values, and the relative bio-availabilities of the ibuprofen has been determined as set forth in Table 2.

TABLE 2

| Preparation | AUC mm$^2$ | Relative Bio-availability | |
|---|---|---|---|
| Commercial dragee | 1466.9 | 1 | 0.79 |
| Capsule according to EP-OS 0 070 714 | 1866.0 | 1.27 | 1 |
| Capsule according to Example 1 | 2270.9 | 1.55 | 1.22 |

TABLE 2-continued

| Preparation | AUC mm$^2$ | Relative Bio-availability | |
|---|---|---|---|
| Capsule according to Example 6 | 2605.0 | 1.78 | 1.40 |

Table 2 shows that the bio-availability of the ibuprofen has been improved by the soft gelatin capsules according to the invention by 55% and 78% over that of the commercially available dragee and by 22% and 40% over that of a previously described capsule preparation. Moreover, as is apparent from the blood level curves of FIGS. 2A through D, there is a more rapid inundation of the active ingredients from the capsules according to the invention than from the previously known preparations. Thus, due to the quicker and higher release and bio-availability of ibuprofen from the capsules according to the invention, there is now provided an Ibuprofen-containing medicament having a better and more rapidly displayed efficiency.

What is claimed is:

1. An ibuprofen-containing soft gelatin capsule containing a solution of from 15 to 30 parts by weight of ibuprofen in from 70 to 85 parts by weight of a polyoxyethylene-polyoxypropylene polymer having a molecular weight of 1400 to 2000.

2. The soft gelatin capsule of claim 1 wherein said solution further contains up to 3 parts by weight of 1,2-propylene glycol.

3. The soft gelatin capsule of claim 1 further comprising up to 40 parts by weight of suspended ibuprofen.

4. The soft gelatin capsule of claim 2 further comprising up to 40 parts by weight of suspended ibuprofen.

5. An ibuprofen-containing soft gelatin capsule containing a solution of from 15 to 30 parts by weight of ibuprofen in from 30 to 76 parts by weight of a polyalkylene glycol and from 7 to 40 parts by weight of a surfactant having a molecular weight of up to 630.

6. The soft gelatin capsule of claim 5 wherein said solution further contains up to 3 parts by weight of 1,2-propylene glycol.

7. The soft gelatin capsule of claim 5 further comprising up to 40 parts by weight of suspended ibuprofen.

8. The soft gelatin capsule of claim 6 further comprising up to 40 parts by weight of suspended ibuprofen.

9. The soft gelatin capsule of claim 5 wherein said surfactant is selected from the group consisting of a polyoxethylene-glycerol trihydroxystearate, a polyoxyethylene ($C_{12-18}$) -fatty alcohol ether, a polyoxyethylene stearate, a polyoxyethylenesorbitan mono ($C_{12-C18}$) fatty acid ester, a polyoxyethylene-polyoxypropylene polymer, having molecular weight of 1400 to 2000 or a mixture thereof.

10. A process for preparing ibuprofen-containing soft gelatin capsules comprising dissolving from 15 to 30 parts by weight of ibuprofen at a temperature of from 45° C. to 65° C. in from 70 to 85 parts by weight of a polyoxyethylene-polyoxypropylene polymer having a molecular weight of 1400 to 2000 to form a solution,
cooling said solution to room temperature, and
incorporating the cooled solution in soft gelatin capsules.

11. The process of claim 10 further comprising adding up to 3 parts by weight of 1,2-propylene glycol to the solution.

12. The process of claim 10 further comprising adding up to 40 parts by weight of suspended ibuprofen to the cooled solution.

13. The process of claim 11 further comprising adding up to 40 parts by weight of suspended ibuprofen to the cooled solution.

14. A process for preparing ibuprofen-containing soft gelatin capsules comprising dissolving from 15 to 30 parts by weight of ibuprofen at a temperature of from 45° C. to 65° C. in a mixture of from 30 to 76 parts by weight of a polyalkylene glycol having a molecular weight of up to 630 and from 7 to 40 parts by weight of a surfactant, to form a solution, cooling said solution to room temperature, and incorporating the cooled solution in soft gelatin capsules.

15. The process of claim 14 further comprising adding up to 3 parts by weight of 1,2-propylene glycol to the solution.

16. The process of claim 14 further comprising adding up to 40 parts by weight of suspended ibuprofen to the cooled solution.

17. The process of claim 15 further comprising adding up to 40 parts by weight of suspended ibuprofen to the cooled solution.

18. The process of claim 14 wherein said surfactant is selected from the group consisting of polyoxyethylene glycerol trihydroxystearate, a polyoxyethylene ($C_{12-18}$)-fatty alcohol ether, polyoxyethylene stearate, a polyoxyethylene sorbitan mono ($C_{12-18}$)-fatty acid ester, a polyoxyethylene-polyoxypropylene polymer having a molecular weight of 1400 to 2000, or a mixture thereof.

* * * * *